(12) United States Patent
Urbano et al.

(10) Patent No.: US 7,789,833 B2
(45) Date of Patent: Sep. 7, 2010

(54) INTEGRATED NERVE STIMULATOR AND ULTRASOUND IMAGING DEVICE

(75) Inventors: Joseph A. Urbano, Audubon, PA (US);
Michael G. Cannon, Haverford, PA (US); Lawrence A. Engle, Stowe, PA (US)

(73) Assignee: Penrith Corporation, Plymouth Meeting, PA (US)

( * ) Notice: Subject to any disclaimer, the term of this patent is extended or adjusted under 35 U.S.C. 154(b) by 737 days.

(21) Appl. No.: 11/560,545

(22) Filed: Nov. 16, 2006

(65) Prior Publication Data

US 2008/0119737 A1 May 22, 2008

(51) Int. Cl.
*A61B 8/00* (2006.01)
*A61B 8/14* (2006.01)
*A61B 5/05* (2006.01)
*A61B 5/04* (2006.01)

(52) U.S. Cl. .............. 600/439; 600/462; 600/554; 600/373; 600/393

(58) Field of Classification Search .............. 600/437, 600/439, 554, 373, 393, 462
See application file for complete search history.

(56) References Cited

U.S. PATENT DOCUMENTS

| | | | |
|---|---|---|---|
| 4,014,437 A | 3/1977 | Rumble et al. | 211/4 |
| 4,157,087 A | 6/1979 | Miller et al. | 128/741 |
| 4,962,766 A | 10/1990 | Herzon | 128/741 |
| 5,919,139 A * | 7/1999 | Lin | 600/443 |
| 6,142,946 A * | 11/2000 | Hwang et al. | 600/459 |
| 6,493,588 B1 | 12/2002 | Malaney et al. | 607/46 |
| 6,533,732 B1 | 3/2003 | Urmey | 600/554 |
| 2006/0085049 A1* | 4/2006 | Cory et al. | 607/48 |

OTHER PUBLICATIONS

From the International Searching Authority, PCT Notification of Transmittal of the International Search Report and the Written Opinion of the International Searching Authority, or the Declaration, International Application No. PCT/US2007/023487, dated May 15, 2008, 8 pages.

* cited by examiner

*Primary Examiner*—Eric F Winakur
*Assistant Examiner*—Katherine L Fernandez
(74) *Attorney, Agent, or Firm*—Woodcock Washburn LLP (57) ABSTRACT

An integrated ultrasound and nerve stimulation system, ultrasound probe and method are provided. The system may include a transcutaneous electrode adapted for external placement on a patient, a percutaneous electrode having an electrically-conducting tip adapted for percutaneous placement proximate a nerve in the patient and a control for causing a current to flow between the electrodes. The system may also include a probe having an ultrasound transducer that transmits ultrasound waves into the patient and receives reflected ultrasound waves from the patient. The probe also has a communication interface for transmitting a signal representative of the received reflected ultrasound waves to a main unit. The main unit is in operative communication with the communication interface and includes a display and a processor, which receives the signal from the probe and causes the display to display an image in accordance with the received signal.

35 Claims, 7 Drawing Sheets

INTEGRATED NERVE STIMULATOR AND ULTRASOUND IMAGING DEVICE

BACKGROUND

Regional nerve blocks are used as an anesthetic technique for surgery and pain control, and can be used in some instances as an alternative to general anesthesia and the complications that often result. For example, general anesthesia requires artificial respiration and often produces post-operative nausea and vomiting that complicate recovery. General anesthesia also includes a risk of post-operative hemodynamic or pulmonary depression, and in some patients it can create post-operative cognitive dysfunction. Regional nerve blocks have been shown to improve anesthesia and analgesia management, and to contribute to earlier ambulation after surgical procedures. In addition, a regional nerve block can provide continuous pain management when needed.

The administration of a regional nerve block involves the injection of an anesthetic to a target nerve, which provides anesthesia to a region distal to that nerve. Unfortunately, locating the target nerve and properly administering the anesthetic can be difficult. For example, a properly administered regional nerve block involves the injection of the anesthetic around—but not into—the target nerve. If the drug is not injected into the area immediately surrounding the nerve, the level of anesthesia required for the intended treatment (e.g., surgery, etc.) may not be achieved. Such a situation delays the procedure and subjects the patient to the risk of inadequate pain control. As noted above, it is also important to avoid inserting the needle directly into the nerve itself because trauma or damage to the nerve may occur. Another challenge involved in the performance of a regional nerve block is avoiding the puncturing of a blood vessel.

A conventional method for locating a target nerve involves the palpation of anatomical landmarks such as muscles, bones and blood vessels by the treatment provider (e.g., a doctor, physician's assistant, nurse, etc.). This method is inexact because of individual variations in patient anatomy and because the target nerve can move as the needle is being inserted. The difficulty in accurately locating the target nerve has been a factor limiting the use of regional nerve blocks.

Ultrasound technology has been used to image various parts of patient's bodies, but the use of an ultrasound imaging device by itself in connection with the administration of regional nerve blocks has met with limited success. For example, a limitation of ultrasound is that it can be difficult in some situations to see the needle or needle tip precisely. It can also be difficult to differentiate the nerve in the image from surrounding structures, such as blood vessels. Also, ultrasound does not provide the level of localization specificity that is provided by the motor or sensory response of Electrical Nerve Stimulation (ENS).

ENS applies an electrical stimulation current across the target nerve to produce a response in the patient such that the treatment provider (i.e., a physician, technician or the like) can accurately locate the nerve. In ENS, the needle that ultimately delivers the anesthetic to the area surrounding the target nerve has a conductive electrode area located at its tip to provide a precise localization of the stimulus. The remainder of the needle is electrically insulated. Another electrode is applied transcutaneously and distal to the needle insertion site. The treatment provider can then cause an electrical current to flow between the electrodes to stimulate the area between the electrodes. If the needle is within a certain distance of the target nerve, the current will cause a response in the nerve, thereby indicating that the needle is in proper position for administration of the anesthetic.

However, conventional ENS also has drawbacks that limit its effectiveness. For example, a treatment provider typically uses palpation or another method to make an educated guess as to the location of the nerve when placing the needle. Thus, additional movement of the needle—which may be uncomfortable for the patient—may be required to place the needle in a proper position for administration of the anesthetic.

Because of the drawbacks of using ultrasound or ENS alone, treatment providers often use both techniques to perform a nerve block. In such an arrangement, the treatment provider uses the ultrasound device to image the nerve—thereby enabling an accurate initial positioning of the needle—and then uses the ENS electrodes to evoke the nerve response to confirm that the needle is in proper position.

Unfortunately, when the two techniques are combined, the treatment provider is required to set up, control and view two separate instrument displays, which is cumbersome and difficult to perform when simultaneously attempting to position a needle in a patient's body. Operating the ultrasound and stimulator controls to perform a nerve block is complicated by the fact that the procedure usually takes place in a sterile field.

For example, a conventional ultrasound machine has a probe that operates within the sterile field and a main unit that operates outside the sterile field. The main unit may be enclosed in a plastic cover to enable it to be located within the sterile field, but in such cases the treatment provider is limited in the adjustments that can be made using the controls of the main unit. More often, a second person may need to operate the main unit while the treatment provider uses the probe. Likewise, a conventional ENS device may include a transcutaneous and percutaneous electrode that operate within the sterile field, and a main unit that operates outside of the sterile field.

Therefore, a treatment provider that uses both an ultrasound and ENS device in connection with a nerve block may need to perform any of the following tasks simultaneously: positioning the ultrasound probe while viewing the ultrasound display, adjusting an ultrasound device setting, positioning the needle, activating the transcutaneous and percutaneous electrodes, adjusting the electrode settings, viewing the electrode settings on a ENS device display and administering the anesthetic. It can be seen that such a wide range of tasks involving more than one medical device (i.e., a separate ultrasound and ENS device) can be extremely difficult for a single person to perform.

Therefore, what is needed is a device that integrates the functionality of an ultrasound and ENS device into a single device. More particularly, what is needed is an integrated ultrasound and ENS device that is adapted for a treatment provider to use while in a sterile field.

SUMMARY

In view of the above limitations and drawbacks, an integrated ultrasound and nerve stimulation system is provided. In addition, an integrated ultrasound and nerve stimulation probe is provided, as well as a method for performing a nerve block on a patient.

The system includes a transcutaneous electrode that is adapted for external placement on a patient and a percutaneous electrode having an electrically-conducting tip adapted for percutaneous placement proximate a nerve in the patient. The system also includes a probe that includes an ultrasound transducer that transmits ultrasound waves into the patient and receives reflected ultrasound waves from the patient, and a control for causing a current to flow between the transcutaneous and percutaneous electrodes. The probe also includes a communication interface for transmitting a signal representative of the received reflected ultrasound waves to a main unit. The main unit, which includes a display and a processor, is in operative communication with the communication interface. The processor receives the signal from the probe and causes the display to display an image in accordance with the received signal.

The method involves placing a transcutaneous electrode on a patient and inserting a percutaneous electrode into the patient and proximate a nerve to be blocked. The method also involves positioning an ultrasound probe on the patient. The probe includes an ultrasound transducer that transmits ultrasound waves into the patient and receives reflected ultrasound waves from the patient. The method further involves operating a control to cause a current to flow between the transcutaneous and percutaneous electrodes to stimulate the nerve.

The probe includes an ultrasound transducer that transmits ultrasound waves into a patient and receives reflected ultrasound waves from the patient. The probe also includes a transcutaneous electrode adapted for external placement on the patient and a percutaneous electrode that has an electrically-conducting tip adapted for percutaneous placement proximate a nerve in the patient. The probe further includes a control that is able to be operated to control the ultrasound transducer and a communication interface for transmitting a signal representative of the received reflected ultrasound waves to a main unit for generation of an image in accordance with the received ultrasound waves.

BRIEF DESCRIPTION OF THE DRAWINGS

The foregoing Summary, as well as the following detailed description, is better understood when read in conjunction with the appended drawings. For the purpose of illustrating various embodiments, there is shown in the drawings example embodiments; however, embodiments are not limited to the specific methods and instrumentalities disclosed. In the drawings.

DETAILED DESCRIPTION OF EXAMPLE EMBODIMENTS

The subject matter of various embodiments is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

To address the limitations and drawbacks of conventional mechanisms for administering a nerve block, various embodiments provide an integrated electrical nerve stimulation and ultrasound imaging system. The ultrasound imaging functions of the system may be designed to image small tissue structures such as blood vessels, nerves and the like in a manner that may be suitable for nerve block applications. For example, the ultrasound imaging capabilities of the system may provide such spatial and contrast resolution that is sufficient to distinguish nerves and blood vessels from surrounding tissue to a degree that is appropriate for the intended application. Additional features, such as the ability to produce an ultrasound image having color flow mode, may be provided.

The system may also be capable of performing electrical stimulation such as, for example, ENS as discussed above. It will be appreciated that ENS is discussed herein as one example of an electrical stimulation technique, and that an embodiment contemplates that the system may be used in connection with any type of electrical stimulation. The system may display information relating to the ENS features of the system on a display where ultrasound information and/or an ultrasound image may also be displayed. In addition, a probe of the system may include ENS controls, and/or the ENS electrodes themselves. The probe may be cordless or corded, depending on the application.

Figure 1A:
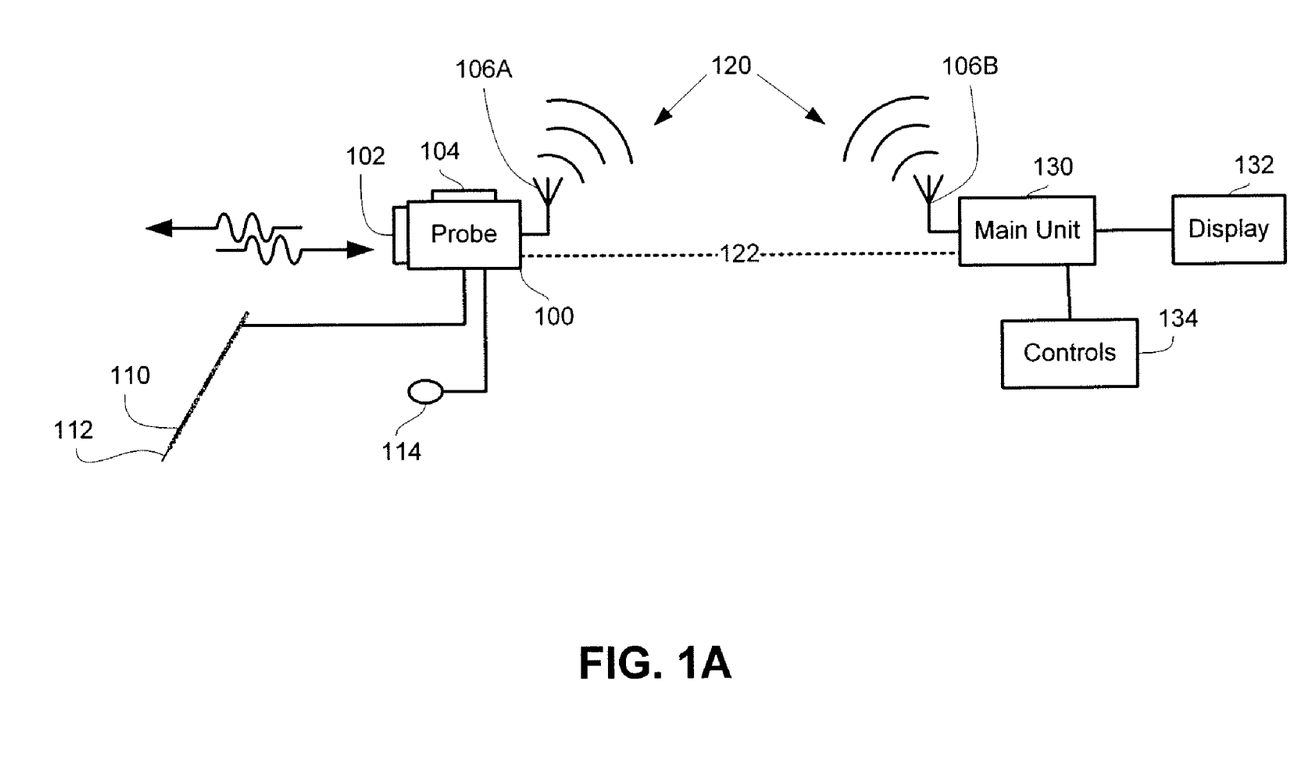
FIGS. 1A-B illustrate two example configurations of an integrated nerve block system according to an embodiment.
Figure 1B:
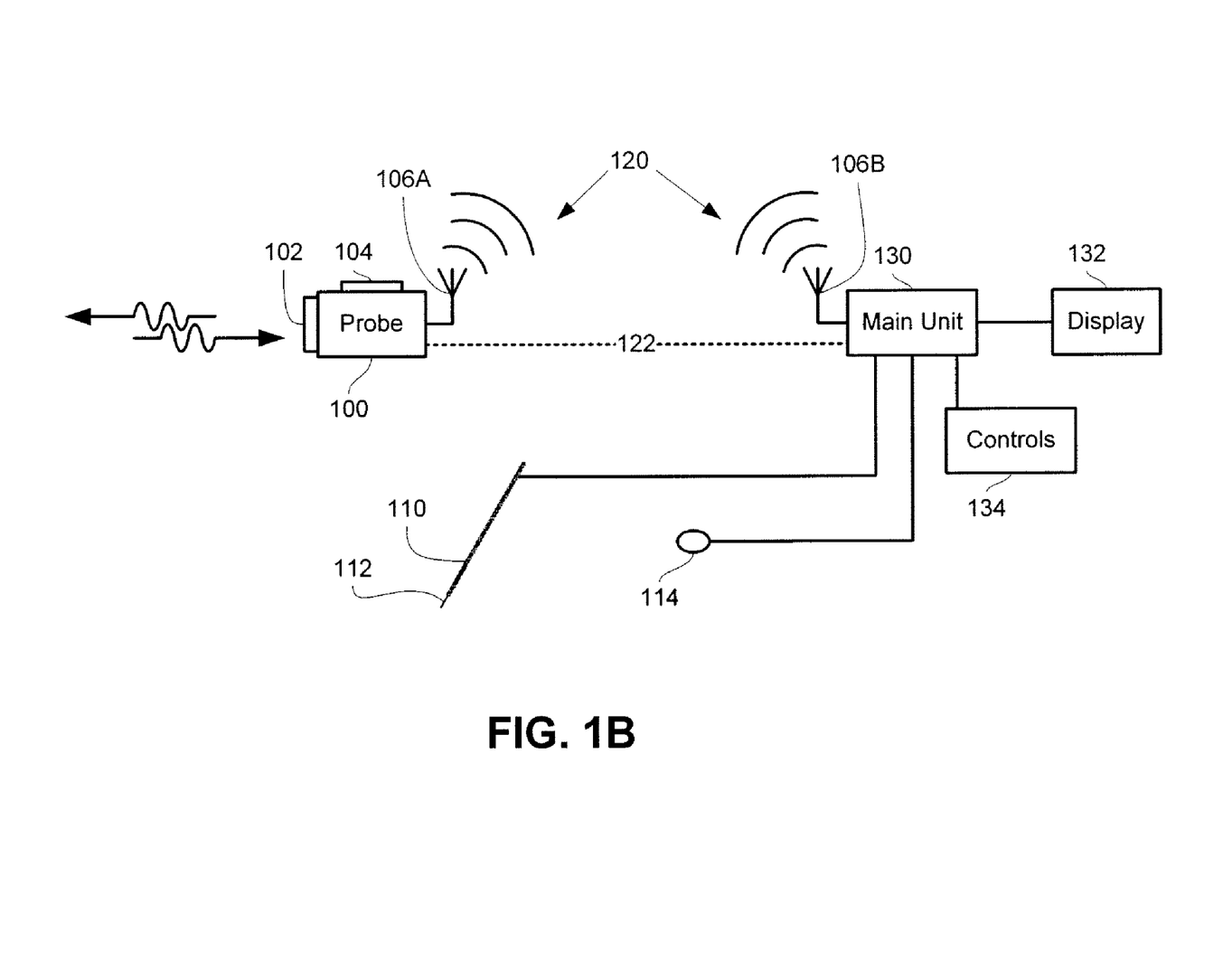

Thus, and referring now to FIGS. 1A-B, two example configurations of an integrated nerve block system are illustrated. It can be seen that in FIG. 1A, percutaneous electrode 110 and transcutaneous electrode 114 are operatively connected to probe 100, whereas in FIG. 1B electrodes 110 and 114 are operatively connected to main unit 130. The example configuration illustrated in FIG. 1B may be used when, for example, electrodes 110 and 114 draw too much power for a battery (not shown in FIGS. 1A-B) in probe 100, when probe 100 is desired to be as small and light as possible, or the like. Thus, in such a situation electrodes 110 and 114 may draw power from main unit 130.

Probe 100 includes ultrasound transducer 102 for transmitting ultrasound energy into a patient and receiving reflected ultrasound energy back from various tissue within the patient's body. The reflected ultrasound energy may be sent to main unit 130 by way of wireless interface 120, which is enabled by antennae 106A-B, or by way of wired interface 122. In an application where high spatial resolution is required, transducer 102 may be an array transducer with a relatively high operating frequency (e.g., approximately 10 MHz or more), high bandwidth (e.g., approximately 80% or more), and fine element pitch (i.e., low $f$-number). In such an embodiment, the ultrasound functions of the system should be capable of operating at these higher frequencies and bandwidths while accommodating a large number of transducer elements (e.g., 128 or more). The contrast resolution may be maximized by methods that increase signal-to-noise ratio (SNR) and, therefore, penetration depth. Such methods may be conventional. The contrast resolution may also be maximized by reducing image artifacts such as those resulting from high sidelobe energy and speckle noise. This may be achieved using advanced beam forming and image filtering (i.e., enhancement) techniques, which also may be conventional.

Probe 100 also includes controls 104, which may include any type or combination of input mechanism. For example, controls 104 may include one or more buttons, switches, glide pads, keys, a mini-joystick, a microphone (e.g., to enable voice recognition), touch-sensitive inputs or the like. Controls 104 may also include an output mechanism such as, for example, Light Emitting Diodes (LEDs), a Liquid Crystal Display (LCD), etc. Controls 104 may control any aspect of ultrasound and/or ENS functions of the system. It will be appreciated that in an embodiment where probe 100 is to be used in a sterile environment, the use of wireless interface 120 to main unit 130 may be preferred, as the use of wireless interface 120 avoids many of the problems associated with having a physical connection between probe 100 and main unit 130 that passes into and out of a sterile field. In an embodiment where wireless interface 120 is used, controls 104 may be capable of being made sterile so as to enable a treatment provider to use controls 104 while performing a nerve block. In one embodiment, such controls are incorporated into a housing (not shown in FIGS. 1A-B) that is disposed around the components of probe 100 that are illustrated in FIGS. 1A-B.

As noted above, in FIG. 1A percutaneous electrode 110 and transcutaneous electrode 114 are operatively connected to probe 100, while in FIG. 1B electrodes 110 and 114 are operatively connected to main unit 130. Although only two configurations of an example system are illustrated above in connection with FIGS. 1A-B, it should be appreciated that other configurations may be used in connection with an embodiment. For example, one of electrodes 110 or 114 may be operatively connected to probe 100, while the other of electrodes 110 or 114 may be operatively connected to main unit 130. Percutaneous electrode 110 includes an electrically-conducting tip 112 that may be used to stimulate a nerve within a patient in accordance with any type of ENS technique. For example, electrodes 110 and 114 may be used as discussed above to cause a current to flow between electrodes 110 and 114, thereby stimulating a nerve that is located near percutaneous electrode 110. In addition to performing ENS duties, percutaneous electrode 110 also may be used as a needle for injecting an anesthetic or other pharmaceutical product into a patent. Thus, percutaneous electrode 110 may be fabricated as part of a hypodermic needle or the like. In either the configuration of FIG. 1A or 1B, the ENS functions of a system may be controlled by either probe 100 or main unit 130, or any combination thereof. Thus, if, for example, electrodes 110 and 114 are operatively connected to probe 100, controls for such electrodes 110 and 114 may be available on probe 100, main unit 130, or both.

It will be appreciated that probe 100 may also include a power supply, such as a battery (not shown in FIGS. 1A-B), for powering ultrasound transducer 102 as well as electrodes 110 and 114. In the example configuration of FIG. 1A, some or all ENS electronics (not shown in FIG. 1A) for controlling and operating electrodes 110 and 114 may be included in probe 100. Although not illustrated in FIGS. 1A-B, a housing may be disposed around any or all of the components illustrated. For example, in the configuration illustrated in FIG. 1A, a housing may be disposed around all components except percutaneous electrode 110 and transcutaneous electrode 114, which may be operatively connected to probe 100 by one or more wires or the like. In an embodiment, some components may be fabricated so as to be part of the housing, or may pass through the housing. For example, transducer 102 may be disposed in an opening of the housing, may be adapted so that part of the housing forms a part of transducer 102, or the like. Any type of configuration of the housing that is appropriate for the intended use of probe 100 is consistent with an embodiment.

Main unit 130 may include display 132 and controls 134. Display may be any type of display device such as, for example, a computer monitor, LCD screen, plasma screen, etc. Display 132 may display information relating to ultrasound operations, as well as information relating to ENS operations. An example screen of information that may be displayed by display 132 is discussed below in connection with FIG. 5.

Figure 2:
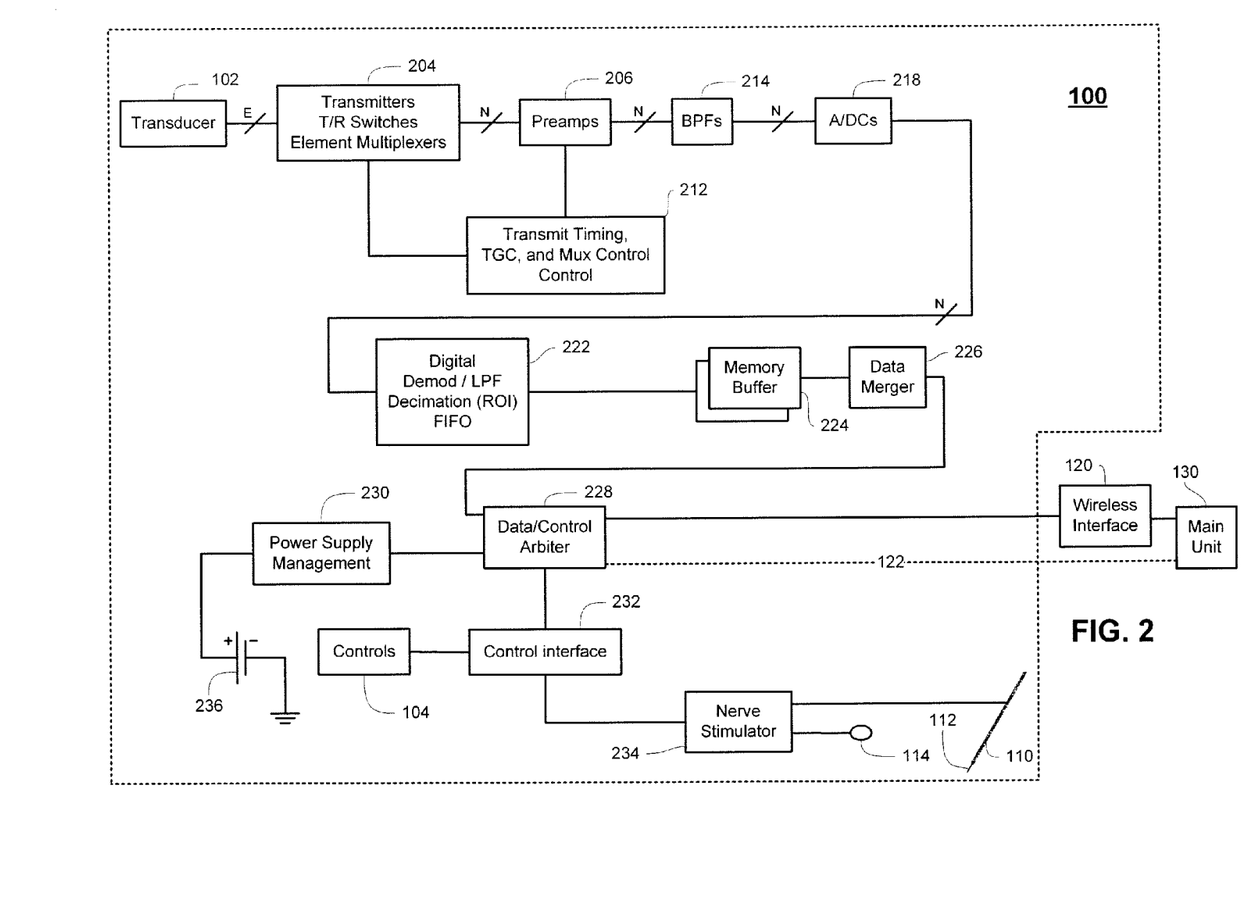
FIG. 2 is a block diagram illustrating various components of an example probe according to one embodiment.

FIG. 2 is a block diagram illustrating various components of an example probe 100 according to one embodiment. As noted above, any or all of the components illustrated in FIG. 2 may be disposed within a housing (not shown in FIG. 2) having any form factor. Probe 100 may include circuitry that is represented in FIG. 2 as a series of blocks, each having a different function with respect to the operation of probe 100. While the following discussion treats each of the blocks as a separate entity, an embodiment contemplates that any or all of such functions may be implemented by hardware and/or software that may be combined or divided into any number of components. For example, in one embodiment the functions represented by any or all of the blocks illustrated in FIG. 2 may be performed by components of a single printed circuit board or the like.

Transducer 102 represents any number of transducer elements that may be present in probe 100. Transducer 102 elements may be comprised of individual transmitter and receiver elements. For example, transmitter 204 includes one or more transmitters that drive each of the transducer elements represented by transducer 102, as well as transmit and/or receive switch circuitry that isolates transmitter 204 from a receiver element (not shown in FIG. 2) during the transmit event. The transmitters may produce a focused, unfocused or defocused transmit beam, depending on the intended application. For example, the focused beam is useful when high peak acoustic pressure is desired as is the case of harmonic imaging. One embodiment uses defocused transmit beams to provide insonfication of a large spatial region as required for synthetic focusing. Such an embodiment also provides a relatively high SNR. The transmit beam may be configured to return information that is sufficient to produce an ultrasound image along an imaging plane—that is, a two-dimensional region within the patient.

Probe 100 receiver circuitry (not shown in FIG. 2) includes a low-noise, high-gain preamplifier 206 for each receive channel (e.g., a Texas Instruments VCA2615 dual-channel variable gain amplifier or the like). Any number of receive channels may be present in an embodiment. Preamplifier 206 may provide variable gain throughout a data acquisition time interval. Preamplifier 206 is followed by bandpass filter 214 to reduce the noise bandwidth prior to analog to digital (A/D) conversion.

The Transmit Timing, TGC and Multiplexer Control 212 provides timing and control of each transmit excitation pulse, element multiplexer setting, and TGC waveform. An example unipolar transmitter channel circuit may include, for example, a transistor functioning as a high-voltage switch followed by a capacitor. The capacitor may be charged to a high voltage (e.g., 100V), and then discharged through the transistor upon excitation by a trigger pulse. Similar transistor-based switches may also be used for transmit/receive isolation, element-to-channel multiplexing, etc. Other embodiments may include more sophisticated transmitters capable of bipolar excitations and/or complex wave shaping and/or the like.

To focus the transmitted ultrasound energy at a desired spatial location, the excitation pulse of each transducer element may be delayed in time relative to the other elements. Such a delay pattern causes the ultrasound waves from all excited elements to combine coherently at a particular point in space. Alternatively, the transmit waveforms may be delayed in such a way as to defocus the beam. This may be beneficial for a system employing synthetic transmit focusing, for example.

A Time-Gain Control (TGC) portion of block 212 provides a programmable analog waveform to adjust the gain of variable gain preamplifier 206. The analog waveform may be controlled by a user through a user interface such as, for example, a set of slide controls used to create a piece-wise linear function. In an embodiment, this piece-wise linear function may be calculated in software, and then programmed into sequential addresses of a digital memory. The digital memory may be read out sequentially at a known time interval beginning shortly after the transmit excitation pulse. The output of the memory may be fed into a digital-to-analog converter (DAC) to generate the analog waveform. In one embodiment, time is proportional to the depth of the ultrasound echoes in the ultrasound receiver. Thus, echoes emanating from tissue deep within a patient's body are attenuated more than those from shallow tissue and, therefore, require increased gain.

One embodiment includes a multiplexer within block 204 for multiplexing a large array of transducer 102 elements (E) into a smaller number of transmit and/or receive channels (N). Such multiplexing allows a smaller ultrasound aperture to slide across a full array on successive transmit events. Both transmit and receive apertures may be reduced to the same number of channels or they may differ from each other. For example, the full array may be used for transmitting while a reduced aperture may be used on receive. Multiplexing also provides for the building of a synthetic receive aperture by acquiring different subsets of the full aperture on successive transmit events. Multiplexing may also provide for the grouping of elements by connecting adjacent elements on either transmit or receive. Grouping by different factors is also possible such as, for example, using a group of three elements on transmit and a group of two elements on receive. Other multiplexing schemes are also possible.

Multiplexing is controlled by means of the Transmit Timing, TGC and Multiplexer Control 212. Various transmit and/or receive elements may be selected when imaging a particular spatial region. For example, ultrasound echo data for an image frame may be acquired by sequentially interrogating adjacent sub-regions of a patient's body until data for the entire image frame has been acquired. In such a case, different sub-apertures (which may include elements numbering less than the full array) may be used for some or all sub-regions. The multiplexer control function may be programmed to select the appropriate sub-aperture (transmit and receive) for each transmit excitation and each image region. The multiplexer control function may also provide control of element grouping as discussed above.

Analog to Digital (A/D) converter 218 converts the analog image data received from probe 100 into digital data using any method, which may be conventional. Digital demodulator 222 may include any type of digital complex mixer, low-pass filter and re-sampler after each A/D converter channel. The digital mixer may modulate the received image data to a frequency other than the center frequency of probe 100. It an embodiment, this function may be performed digitally rather than in the analog or sampling domains to provide optimum flexibility and minimal analog circuit complexity. The low-pass filter reduces the signal bandwidth after mixing and before re-sampling when a lower sampling rate is desired. One embodiment uses quadrature sampling at A/D converter 218 and, therefore, such an embodiment does not require a quadrature mixer to translate the radio frequency (RF) signals of transducer 102 to a baseband frequency. However, complex demodulation by means of an analog or digital mixer or the like may also be used in connection with an embodiment.

Memory buffer 224 may have sufficient storage capacity to store up to, for example, two frames of data. Such a frame-sized buffer 224 allows frames to be acquired at a rate substantially higher than the rate at which frames can be transferred to main unit 130 across wireless interface 120, for example. Such a configuration may, in an embodiment, be preferable to acquiring each frame over a longer time interval because a longer time interval could reduce the coherence of the acquired data throughout the frame. If frame transmission rates are as least as fast as frame acquisition rates, a smaller memory buffer 224 may be used. One embodiment uses a single ping-pong buffer fed by all receiver channels as memory buffer 224. Data from multiple channels may be time interleaved into memory buffer 224. For example, 32 receiver channels each sampled at the rate of 6 MHz would produce a total baseband data rate of 192M words per second, which is well within the rates of conventional DDR2 SDRAM. The ping-pong nature of memory buffer 224 may allow new data to fill buffer 224 while previously acquired data is read from memory and sent to wireless interface 120.

Memory buffer 224 is followed by data merger 226 that merges the receive channel data into one or more data streams before advancing the data stream to wireless interface 120 for transmission to main unit 130. Data from data merger 226 may be sent across wireless interface 120 (or, alternately, across wired interface 122) at a rate that is appropriate for the transmission medium. The data from all receive channels may be multiplexed in some fashion prior to transmission over wireless interface 120 or wired interface 122. For example, time-division multiplexing (TDM) may be used. Other types of multiplexing are also possible such as, for example, frequency-division multiplexing (FDM), code-division multiplexing (CDM) or some combination of these or other multiplexing techniques.

In addition to image data transfer, control information may be transferred between probe 100 and main unit 130, preferably over the same communication link, such as wireless interface 120 and/or wired interface 122. Control commands may be sent from main unit 130 to probe 100 to instruct the mode of operation or various imaging parameters such as maximum imaging depth, sampling rate, element multiplexing configuration, etc. Also, control commands may be sent from probe 100 to main unit 130 to communicate probe-based user controls 104 (e.g., button pushes) and probe operational status (e.g., battery level from power supply management 230).

In an embodiment, data/control arbiter 228 is responsible for merging control information and image data sent from probe 100 to main unit 130. The control information may be passed from control interface 232, where it is collected to data/control arbiter 228 for transmission to main unit 130. The control and image data may be distinguishable from each other when sent across wireless interface 120 or wired interface 122 to facilitate proper handling at main unit 130. In addition, data/control arbiter 228 may accept control commands from main unit 130 and respond by appropriate programming of probe 100 circuitry, memory-based tables, registers, etc.

Probe 100 circuitry also includes power supply 236 to provide drive voltage to the transmitters and/or power to other electronic circuitry. Power supply 236 may be any type of electrical power storage mechanism, such as one or more batteries or other devices. In one embodiment, power supply 236 may be capable of providing approximately 100V DC under typical transmitter load conditions and may also be designed to be small and light enough to fit inside a housing of probe 100, if configured to be hand held by a treatment provider or the like. In addition, power supply management circuitry 230 may also be provided to manage the power provided by power supply 236 to both the ultrasound-related circuits as well as nerve stimulator 234 circuits (if applicable).

As noted above in connection with FIGS. 1A-B, controls 104 may be provided to control ultrasound and/or nerve stimulator 234 functions of probe 100. Control interface 232 may pass user input received from controls 104 to data/control arbiter 228 for processing and action, if necessary. In addition to sending data to main unit 130, wireless interface 120 may also receive control or other information from main unit 130. This information may include, for example, image acquisition parameters, look-up tables and programming code for field programmable gate arrays (FPGAs) or microcontrollers residing in probe 100, or the like. Controller interface 232 within probe 100 accepts and interprets commands from main unit 130 and configures probe 100 circuitry accordingly.

As in the example configuration of FIG. 1A, FIG. 2 illustrates an embodiment where nerve stimulator 234 is part of probe 100. In such an embodiment, percutaneous electrode 110 having electrically-conducting tip 112, as well as transcutaneous electrode 114, may be operatively connected to probe 100 by way of one or more wires or the like. In addition, one or more of the components illustrated below in connection with FIG. 4 may be located in probe 100 as well.

Now that an example configuration of components of probe 100 has been described, an example configuration of components of main unit 130 will be discussed with reference to FIG. 3. It should be noted that any or all of the components illustrated in FIG. 3 may be disposed within one or more housings (not shown in FIG. 3) having any form factor.

As discussed above, probe 100 may be operatively connected to main unit 130 by way of wireless interface 120 and/or wired interface 122. It will be appreciated that in an embodiment most data transfer occurs from probe 100 to main unit 130. That is, large amounts of image data sent from probe 100 may be received by main unit 130 while control information or the like (e.g., ultrasound, nerve stimulator 234 may be sent from main unit 130 to probe 100). Control information is managed and, in many cases, generated by CPU controller 332. CPU controller 332 may also be responsible for configuring circuitry of main unit 130 for an active mode of operation with required setup parameters.

In an embodiment, data/control arbiter 310 may be responsible for extracting control information from the data stream received by wireless interface 120 or wired interface 122 and passing it to CPU 332 while sending image data from the data stream to input buffer 312. Data/control arbiter 310 may also receive control information from CPU 332, and may transfer the control information to probe 100 via wireless interface 120 or wired interface 122.

A user, such as a treatment provider or the like, may control the operations of main unit 130 using control panel 330. Control panel 330 may be any type of input or output device, such as a keyboard, mouse, trackball, etc. Main unit 130 may be powered by any type of power supply (not shown in FIG. 3) such as, for example, a 120 VAC outlet, a battery, etc.

To facilitate the pixelforming process that ultimately generates an ultrasound image from the image data received from probe 100, the incoming image data may be stored in input buffer 312. In an embodiment, input buffer 312 may be capable of storing up to approximately two frames of data, for example, and may operate in a "ping-pong" fashion whereby a previously received frame of data is processed by pixelformer 322 while a new incoming frame is written to another page of memory in input buffer 312. Pixelformer 322 may be any combination of hardware and/or software that is capable of transforming raw image data received from each receive channel and each transmit event (from probe 100) into a pixel-based image format. This may be performed by coherently combining data from various transmit and receive elements, or groups of elements, to form an image focused optimally at each pixel. Many variations of this approach may be used in connection with an embodiment. Alternately, this function may include a beamformer that focuses samples along beam directions. The focused sample data then may be converted to a raster format for display on display 350.

Once a frame of complex pixel data has been formed, it is stored in frame buffer 324 for use by either flow estimator 326 or image processor 328. In an embodiment, flow estimator 326 uses, for example, Doppler or cross-correlation methods to determine one or more flow characteristics from the received image (ultrasound echo) data. Once the flow estimation parameters have been computed, they may be encoded into data values and either stored in frame buffer 324 for access by image processor 328 or sent directly to image processor 328.

Spectral Doppler Processor (SDP) 320 may receive focused baseband data from pixelformer 322 from one or more spatial locations within the image region in a periodic or other fashion. The spatial locations are referred to herein as range gates. SDP 320 performs high-pass filtering on the data to remove signal contributions from slow moving tissue or the like. The remaining, higher frequency signals from blood flow (i.e., from blood vessels, which sometimes resemble nerves) are in the normal audio frequency range and these signals may be conventionally presented as an audible signal by speaker 318, thereby assisting a treatment provider in discerning an intended nerve from a blood vessel, for example. SDP 320 may also perform spectral analysis via a Discrete Fourier Transform computation, or other means, to create an image representing a continuously updated flow velocity display (i.e., a time-varying spectrogram of the blood flow signal). The velocity data may be sent through image processor 328 for further processing and display.

A user of main unit 130 may use microphone 314 for controlling main unit 130 using, for example, voice recognition technology. Alternately, or in addition to using microphone 314 for control purposes, a user may use microphone 314 for taking notes while examining or placing a nerve block in a patient. Audio notes may be saved separate from, or along with, video data.

Audio codec 316 may accept audio data input from microphone 314 and interfaces with CPU 332 so audio data received by audio codec 316 may be stored and/or interpreted by CPU 332. Such audio interpretation may facilitate system control by way of, for example, voice commands from a user of main unit 130. For example, frequently-used system commands may be made available via voice control. (Such commands may also be made available by way of control panel 330). Audio storage facilitates audio annotation of studies for recording patient information, physician notes and the like.

The audio data may first be converted to a compressed format such as MP3 before storing in, for example, storage 338. Other standard, proprietary, compressed or uncompressed formats may also be used in connection with an embodiment. Speaker 318 may provide audio output for reviewing stored annotation or for user prompts from main unit 130 resulting from error conditions, warnings, notifications, etc. In one embodiment, a representation of the Doppler shift caused by moving reflectors may be output to speaker 318 for user guidance in range gate or steering line placement and vessel identification.

Video interface 334 connects image processor 328 to display 350 by way of CPU 332. Display 350 may be any device that is capable of presenting visual information to a user of main unit 130 such as, for example, an LCD flat panel, CRT monitor, composite video display or the like. Video data may also be sent to storage 338, which may be a VCR, disk drive, USB drive, CD-ROM, DVD or other storage device. Prior to storage, still image frames of data may be encoded in a compressed format such as JPEG, JPEG2000 or the like. Image clips or sequences may be encoded in a format such as MJPEG, MJPEG2000 or a format that includes temporal compression such as MPEG. Other standard or proprietary formats may be used as well.

Image processor 328 may accept either complex or detected tissue image data and then filter it temporally (i.e., frame to frame) and spatially to enhance image quality by improving contrast resolution (e.g., by reducing acoustic speckle artifact) and by improving SNR (e.g., by removing random noise). Image processor 328 may also receive flow data and merge it with such tissue data to create a resultant image containing both tissue and flow information. To accomplish this, image processor 328 may use an arbitration process to determine whether each pixel includes flow information or tissue information. Pixels may also be overwritten by graphical or textual information. In an embodiment, both the flow arbitration and graphical overlay occur just prior to image display to allow the tissue and flow images to be processed independently.

Temporal filtering typically is performed on both the tissue and flow data prior to merging the data. Temporal filtering can yield significant improvements in SNR and contrast resolution of the tissue image and reduced variance of the flow image while still achieving a final displayed temporal resolution suitable for clinical diagnosis. As a result, relatively higher levels of synthetic aperture (spatial) subsampling may be provided, thereby reducing the number of transmit events (and, consequently, the power consumption of probe 100). Temporal filtering typically involves filtering data from frame to frame using either an FIR or IIR-type filter. In one embodiment, a simple frame averaging method may be used as discussed below, for example.

Temporal filtering or tissue persistence is commonly applied to frames of ultrasound data. When the acquisition frame rate exceeds the rate of motion of anatomical structures, low-pass filtering across frames can reduce random additive noise while preserving or enhancing image structures. Also, minute degrees of motion—commonly due to patient or operator movement—help to reduce image speckle, which is caused by the interference of acoustic energy from randomly distributed scatterers that are too small to be resolved with the frequency range of ultrasound probe 100. Speckle is coherent by its nature so, in the absence of motion, it will produce the same pseudo-random noise pattern on each image frame. However, small amounts of motion diversify the speckle enough to make low-pass filtering across frames effective at reducing it.

A simple method of temporal filtering is averaging neighboring frames. An example of the recursive version of a moving-average filter is described as follows where $X(n)$ is the input frame acquired at time n, $Y(n)$ is the corresponding output frame, and k is a frame delay factor that sets the size of the averaging window:

$$Y(n)=Y(n-1)+X(n)-X(n-k) \quad (1)$$

Another simple low-pass filter is a first-order IIR filter of the form:

$$Y(n)=C \times Y(n-1)+(1-C) \times X(n) \quad (2)$$

In such an embodiment, the coefficient C sets the filter's time constant and the degree of low-pass filtering applied to the frame sequence. It should be appreciated that Equations (1) and (2) are just examples of possible filters and filtering techniques that may be used in connection with an embodiment.

Control panel 330 provides buttons, knobs, etc., to allow the user to interact with the system by changing modes, adjusting imaging parameters, nerve stimulator parameters and so forth. Control panel 330 may be operatively connected to CPU 332 by way of, for example, a simple low bandwidth serial interface or the like. Main unit 130 may also include one or more I/O interfaces 336 for communication with other devices, computers, a network or the like by way of a computer interface such as USB, USB2, Ethernet or WiFi wireless networking, for example. Such interfaces allow image data or reports to be transferred to a computer or external storage device (e.g., disk drive, CD-ROM or DVD drive, USB drive, flash memory, etc.) for later review or archiving, and may allow an external computer or user to control main unit 130 remotely.

Figure 3:
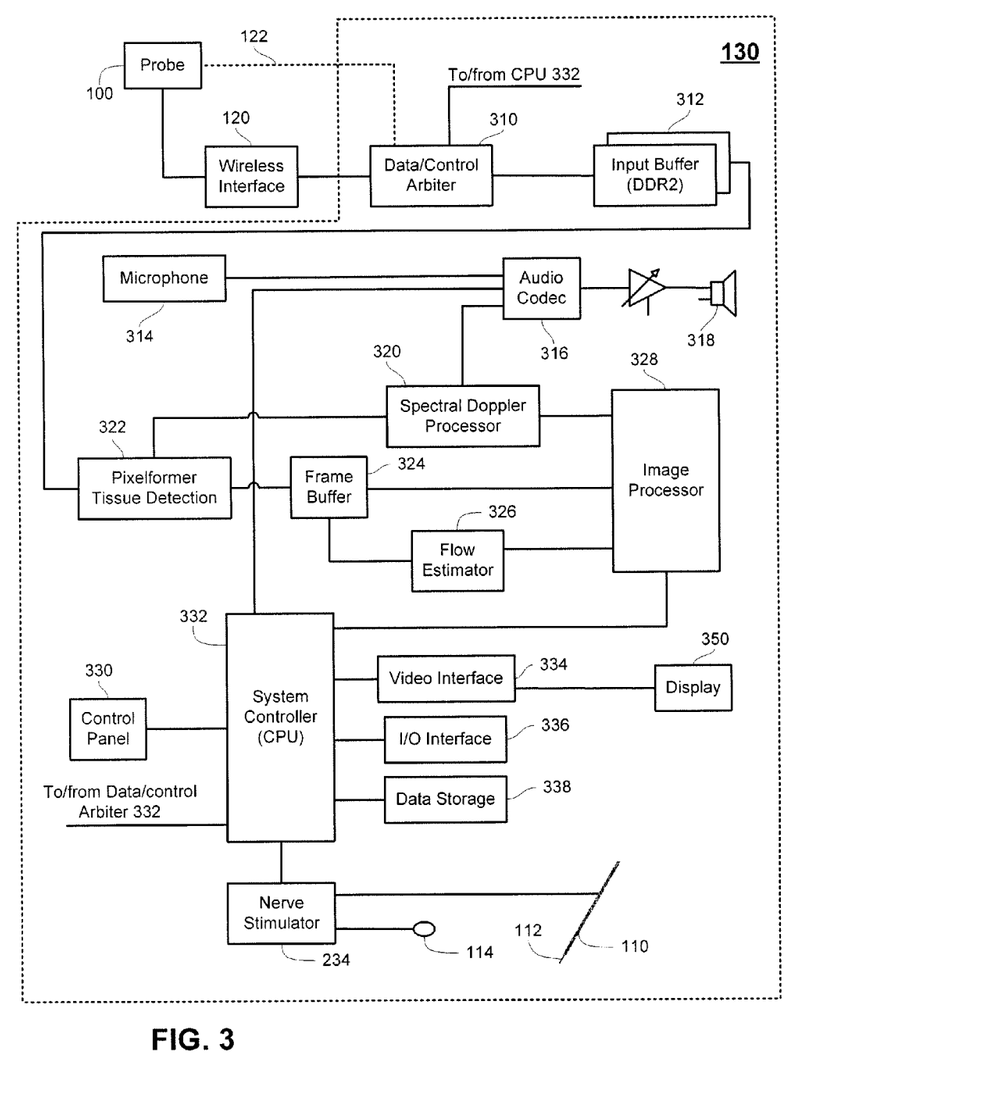
FIG. 3 is a block diagram illustrating various components of an example main unit according to one embodiment.

FIG. 3 illustrates a configuration discussed above in connection with FIG. 1B, where nerve stimulator 234 (as well as percutaneous electrode 110 with electrically-conducting tip 112 and transcutaneous electrode 114) is a part of main unit 130 instead of probe 100. It will be appreciated that main unit 130 may be adapted to operate in the configuration discussed above in connection with FIG. 1A, where nerve stimulator 234 is a part of probe 100, or to some other configuration.

Figure 4:
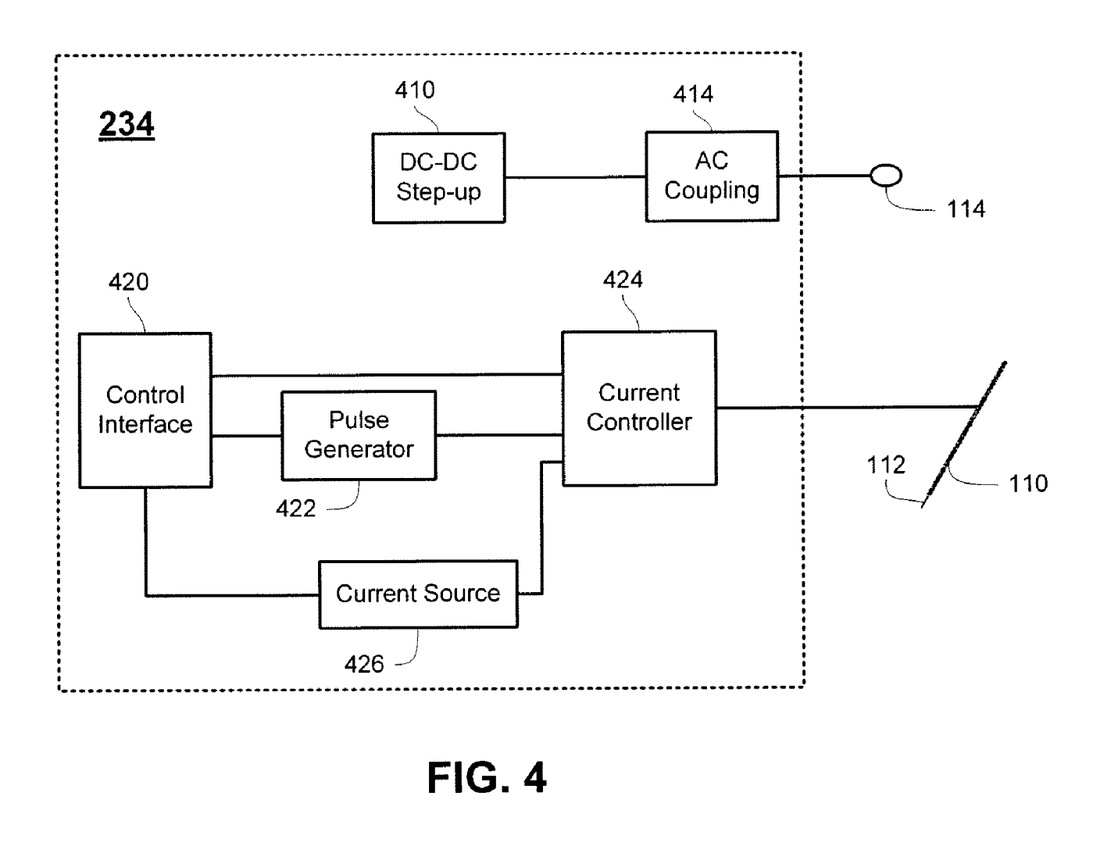
FIG. 4 is a block diagram illustrating various components of an example nerve stimulator according to one embodiment.

Now that an example probe 100 and main unit 130 have been described, FIG. 4 illustrates various components of an example nerve stimulator 234 according to one embodiment. As discussed above, nerve stimulator 234 includes percutaneous electrode 110 with electrically-conducting tip 112 and transcutaneous electrode 114. In an embodiment involving the guidance of a regional nerve block whereby an anesthetic is injected into a region of tissue surrounding a nerve, the needle may act as percutaneous electrode 110. In such an embodiment, the hub and shaft of the needle may be sufficiently insulated to avoid leakage of stimulation current to surrounding tissue, while electrically-conducting tip 112 is located in a very small area to ensure precise localization of the stimulus.

DC-DC step up 410 may adapt the power signal that is received from, for example, power supply 236 of probe 100 as discussed above in connection with FIG. 2 (in a configuration as depicted above in connection with FIG. 1A) or from a power supply of main unit 130 as discussed above in connection with FIG. 3 (in a configuration as depicted above in connection with FIG. 1B) to a signal that is appropriate for transcutaneous electrode 114 and/or percutaneous electrode 110. AC coupling 414 may be implemented by, for example, a capacitor or other mechanism. AC coupling 414 may allow AC current and block DC current from flowing through a patient's body via transcutaneous electrode 114.

In an embodiment, nerve stimulator 234 includes control interface 420 that carries out operating parameter adjustments as received from a user of nerve stimulator 234, or from a component of main unit 130 or probe 100. Depending on the configuration (e.g., whether nerve stimulator is part of probe 100 or main unit 130), such controls may be integrated with control panel 330 of main unit 130 (see FIG. 3) or all or some of the controls may be located in or on a housing of probe 100. In one embodiment, the controls may be operated via voice commands from the user (e.g., using microphone 314 of main unit 130). It will be appreciated that additional software or hardware components may be installed in main unit 130 to carry out voice recognition to enable such voice control.

In an embodiment, an indication of actual flowing current or other operating parameters may be provided. Such indications may include, for example, open circuit, high impedance and polarity conditions. The indications may be displayed on display 350 of main unit 130 and/or a display built into a housing of probe 100.

One example of a stimulator control is that of an adjustable constant current source 426 as shown in FIG. 4. In an embodiment, current source 426 may provide an operating range of 0-10 kΩ output impedance to compensate for variations in tissue impedance. Stimulus amplitude may be controlled in a range of 0-5 mA. In one embodiment, a monophasic rectangular output pulse is used, and may have a selectable duration of 0.1-1.0 ms. In such an embodiment, the longer durations may be used primarily for pain fibers and the shorter durations for motor fibers. The pulse rate may be approximately 1-2 Hz, for example. Pulse generator 422 generates a periodic pulse with user-selected attributes. The amplitude, pulse width and frequency of the pulses may be variable if other applications are supported by nerve stimulator 234. Ultimately, current controller 424 outputs the current to electrically-conducting tip 112 of percutaneous probe 110.

In one embodiment, in addition to the user controls and display, some or all of nerve stimulator 234 components may be shared with other devices. For example, the power source for nerve stimulator 234 may be shared with ultrasound circuitry in probe 100 or main unit 130. Also, control interface 420 and pulse generator 422 may be implemented digitally and integrated into a programmable logic component that is also used for ultrasound-related functionality. An example of a programmable logic component is a Field Programmable Gate Array (FPGA) such as the Cyclone II family of devices available from Altera Corporation.

Figure 5:
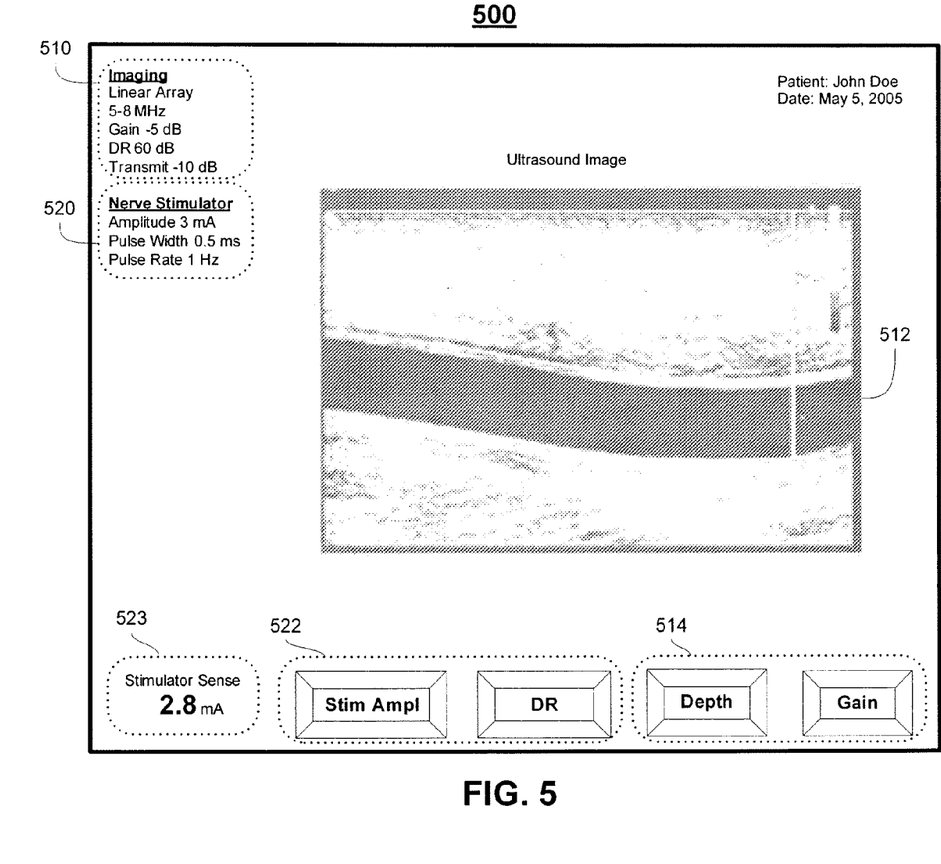
FIG. 5 is an example screen of an incorporated ultrasound and nerve stimulation display according to one embodiment.

Now that the various components of probe 100, main unit 130 and nerve stimulator 234 have been described, FIG. 5 illustrates an example screen 500 of an incorporated ultrasound and nerve stimulation display according to one embodiment. It will be appreciated that screen 500 may be displayed on, for example, display 350 of main unit 130 as discussed above in connection with FIG. 3.

Screen 500 may include ultrasound image 512 of the region of interest, as well as ultrasound imaging parameters 510. Image 512 may be a visual representation of received echo ultrasound information from a patient. Image 512 may represent such data along an imaging plane, which, as noted above, is a two-dimensional "slice" representing a cross-sectional image of the imaged region within the patient. Ultrasound imaging parameters 510 may include any type of information that may be relevant to ultrasound image 512. Screen 500 may also include on-screen ultrasound imaging controls 514 for modifying one or more ultrasound operating parameters.

In addition to the ultrasound imaging information discussed above, screen 500 may also include information relating to nerve stimulator 234. For example, screen 500 may include nerve stimulator parameters 520, which may include any type of information relating to the operation of nerve stimulator 234. In addition, screen 500 may include on-screen nerve stimulator controls 522 that may be used to modify the operation of nerve stimulator 234. Furthermore, screen 500 may provide a real-time, continuously updated display of nerve stimulator status data 523 (e.g., stimulator sense current). Thus, an embodiment provides a combined display of ultrasound and nerve stimulator 234 information.

Figure 6:
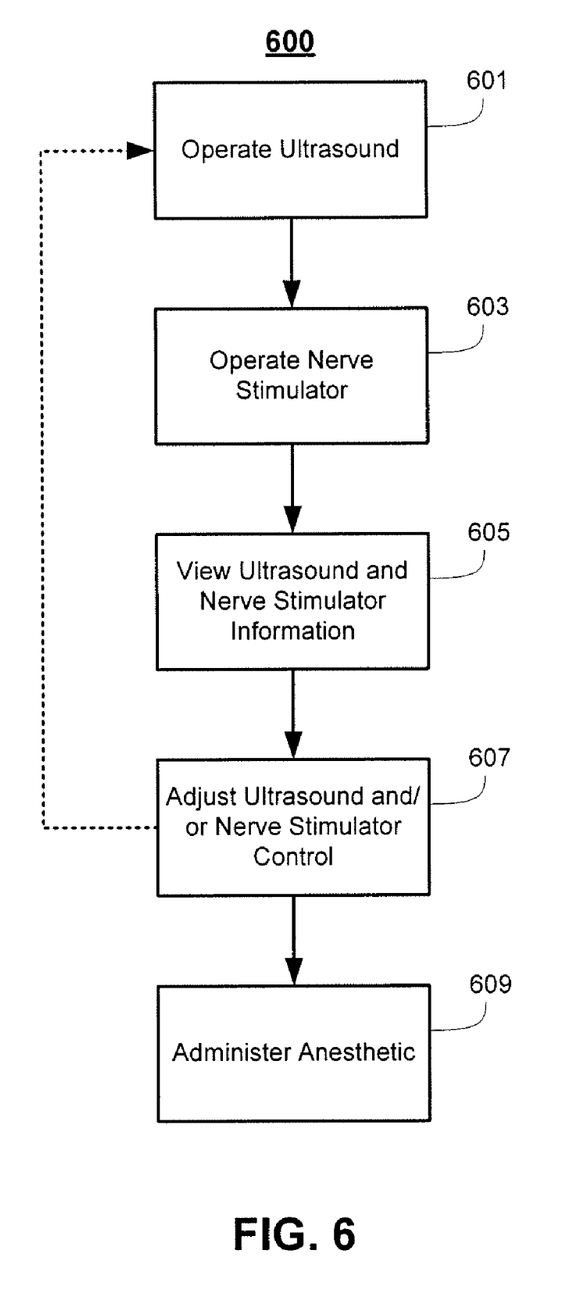
FIG. 6 is a flowchart illustrating an example method of administering a nerve block according to one embodiment.

FIG. 6 is a flowchart illustrating an example method 600 of administering a nerve block according to one embodiment. References will be made to the preceding figures as appropriate. At step 601, a user operates the ultrasound functions of the system. Such operation may include positioning probe 100, setting or adjusting operating parameters and the like so as to cause an ultrasound image to be displayed by display 350.

At step 603, a user operates the nerve stimulator 234 functions of the system. Such operation may include placing transcutaneous electrode 114 and positioning electrically-conducting tip 112 of percutaneous electrode 110 (e.g., by inserting the needle of which percutaneous electrode 110 is a part into a patient proximate the nerve block site). Such placement of percutaneous electrode 110 may be made after referring to the ultrasound image generated above in step 601, thereby enabling a user to position percutaneous electrode 110 very close to the intended nerve block site. Step 603 may also include the passing of current between transcutaneous electrode 114 and electrically-conducting tip 112 of percutaneous electrode 110 to stimulate, and therefore precisely locate, the intended nerve to be blocked. The passing of current may be skipped if step 603 is carried out during the initial placement of electrodes 110 and 112 (if, for example, steps 601-607 will be repeated).

At step 605, a user views ultrasound and nerve stimulator 234 information on, for example, display 350 of main unit 130. Alternately, probe 100 may display both ultrasound and nerve stimulator 234 information. At step 607, a user may adjust an ultrasound and/or nerve stimulator 234 control using, for example, control 104 of probe 100, control panel 300 of main unit 130, and/or the like. It will be appreciated that the user may not need to adjust any controls (if, for example, step 605 has already been performed and step 603 has been repeated and the nerve stimulation has successfully located the target nerve), or may repeat steps 601-607 as many times as necessary to properly position transcutaneous electrode 114 and electrically-conducting tip 112 of percutaneous electrode 110 (as indicated by the dotted line in FIG. 6). At step 609, the user administers an anesthetic to perform the nerve block. As noted above, a hypodermic needle of which percutaneous electrode 110 is a part, or the like, may be used to administer the anesthetic. It should be appreciated that the ultrasound image may be viewed during the administration of anesthetic to monitor the flow of anesthetic around the nerve site, and the position of the hypodermic needle adjusted accordingly.

While the various embodiments have been described in connection with the embodiments of the various figures, it is to be understood that other similar embodiments may be used or modifications and additions may be made to the described embodiments for performing the same function of the various embodiments without deviating therefrom. Therefore, the embodiments should not be limited to any single embodiment, but rather should be construed in breadth and scope in accordance with the appended claims.

What is claimed:

1. An ultrasound imaging and electrical stimulation system, comprising:
a transcutaneous electrode adapted for external placement on a patient;
a percutaneous electrode having an electrically-conducting tip adapted for percutaneous placement proximate a nerve in the patient;
a probe comprising:
an ultrasound transducer that transmits ultrasound waves into the patient and receives reflected ultrasound waves from the patient;
a communication interface, the communication interface transmitting a signal representative of the received reflected ultrasound waves to a main unit;
an enclosure; and
a first control, the first control causing a current to flow between the transcutaneous and percutaneous electrodes, and the first control being at least partially disposed within the enclosure, and
wherein the main unit is in operative communication with the communication interface, and wherein the main unit comprises a display and a processor, wherein the processor receives the signal from the probe and causes the display to display an image in accordance with the received signal.

2. The system of claim 1, wherein the main unit further comprises a second control, the second control causing the current to flow between the transcutaneous and percutaneous electrodes.

3. The system of claim 1, wherein the transcutaneous and percutaneous electrodes are operatively connected to the probe.

4. The system of claim 1, wherein the transcutaneous and percutaneous electrodes are operatively connected to the main unit.

5. The system of claim 1, wherein the display further displays control information relating to the transcutaneous and percutaneous electrodes.

6. The system of claim 1, wherein the display further displays control information relating to an ultrasound operating condition.

7. The system of claim 1, wherein the communication interface is a wireless communication interface.

8. The system of claim 1, wherein the probe receives control information from the main unit via the communication interface.

9. The system of claim 1, wherein the probe further comprises a power supply that powers the transducer and communication interface.

10. The system of claim 9, wherein the power supply further powers the transcutaneous and percutaneous electrodes.

11. The system of claim 1, wherein the main unit further comprises a speaker that outputs an audible representation of a Doppler shift determined from the signal.

12. The system of claim 1, wherein the main unit further comprises a microphone for receiving audio information from a user.

13. The system of claim 1, wherein the main unit further comprises a control interface that enables a user to control the main unit.

14. The system of claim 1, wherein the probe is adapted for use in a sterile field.

15. The system of claim 1, wherein the percutaneous electrode is formed as part of a hypodermic needle that is adapted to inject an anesthetic proximate the nerve.

16. The system of claim 1, wherein the current is adapted to induce a response from the nerve.

17. The system of claim 1, wherein at least one of the ultrasound transducer or the communication interface is at least partially disposed within the enclosure.

18. The system of claim 1, wherein the first control includes at least one input, the at least one input being disposed proximate to an external surface of the enclosure.

19. A method for performing a nerve block on a patient, the method comprising:
placing a transcutaneous electrode on the patient;
inserting a percutaneous electrode into the patient and proximate a nerve to be blocked;
positioning an ultrasound probe on the patient, the ultrasound probe comprising:
an ultrasound transducer that transmits ultrasound waves into the patient and receives reflected ultrasound waves from the patient;
an enclosure; and
a first control, the first control causing a current to flow between the transcutaneous and percutaneous electrodes to stimulate the nerve, and the first control being at least partially disposed within the enclosure;
transmitting via a communications interface a signal representative of the received reflected ultrasound waves to a main unit;
operating the first control to cause the current to flow between the transcutaneous and percutaneous electrodes to stimulate the nerve; and
administrating the nerve block.

20. The method of claim 19, further comprising viewing an ultrasound image that represents a region of the patient as represented by the received reflected ultrasound waves on a display of a main unit that is operatively connected to the probe.

21. The method of claim 20, wherein the main unit comprises a second control, the second control causing the current to flow between the transcutaneous and percutaneous electrodes to stimulate the nerve.

22. The method of claim 20, further comprising viewing control information relating to the ultrasound image on the display.

23. The method of claim 19, further comprising viewing control information relating to the transcutaneous and percutaneous electrodes on the display.

24. The method of claim 19, further comprising operating the control to adjust the operation of the ultrasound transducer.

25. The method of claim 19, in which the administrating the nerve block further comprises injecting an anesthetic proximate the nerve using a hypodermic needle of which the percutaneous electrode is a part.

26. The method of claim 25, wherein the injection of the anesthetic is performed in accordance with information displayed in the ultrasound image and the response of the nerve.

27. The method of claim 19, wherein the ultrasound transducer is at least partially disposed within the enclosure.

28. An ultrasound probe, comprising:
an ultrasound transducer that transmits ultrasound waves into a patient and receives reflected ultrasound waves from the patient;
a transcutaneous electrode interface adapted for connection to a transcutaneous electrode;

a percutaneous electrode interface adapted for connection to a percutaneous electrode;

an enclosure;

a control, the control being at least partially disposed within the enclosure and the control being operable to:
control the ultrasound transducer, and
cause a current to flow between the transcutaneous electrode interface and percutaneous electrode interface; and a communication interface for transmitting a signal representative of the received reflected ultrasound waves to a main unit for generation of an image in accordance with the received ultrasound waves.

29. The probe of claim 28, wherein the communication interface is a wireless communication interface.

30. The probe of claim 28, wherein the communication interface receives control information from the main unit.

31. The probe of claim 28, wherein the probe further comprises a power supply that powers the transducer and communication interface.

32. The probe of claim 31, wherein the power supply further powers the transcutaneous electrode interface and percutaneous electrode interface.

33. The probe of claim 28, wherein the probe is adapted for use in a sterile field.

34. The probe of claim 28, wherein the current is adapted to induce a response from a nerve.

35. The probe of claim 28, wherein at least one of the ultrasound transducer, the communications interface, the transcutaneous electrode interface, or the percutaneous electrode interface is at least partially disposed within the enclosure.

* * * * *